(12) United States Patent
Stevenson et al.

(10) Patent No.: US 7,699,873 B2
(45) Date of Patent: Apr. 20, 2010

(54) SPINOUS PROCESS ANCHORING SYSTEMS AND METHODS

(75) Inventors: Kevin Stevenson, Atlanta, GA (US); Robert A. Farris, Cordova, TN (US); Jason May, Memphis, TN (US)

(73) Assignee: Warsaw Orthopedic, Inc.

( * ) Notice: Subject to any disclaimer, the term of this patent is extended or adjusted under 35 U.S.C. 154(b) by 1032 days.

(21) Appl. No.: 11/287,517

(22) Filed: Nov. 23, 2005

(65) Prior Publication Data
US 2007/0118120 A1   May 24, 2007

(51) Int. Cl.
A61B 17/70 (2006.01)
(52) U.S. Cl. ........................ 606/250; 606/248; 606/251; 606/252; 606/253; 606/279
(58) Field of Classification Search .................. 606/248, 606/279, 246, 247, 249, 250, 251, 252, 253, 606/254, 255, 256, 257, 258, 259, 260, 261, 606/262, 263, 264, 265, 266, 267, 268, 269, 606/270, 271, 272, 273, 274, 275, 276, 277, 606/278, 300–320, 322–331; 403/62, 177; 623/17.11
See application file for complete search history.

(56) References Cited

U.S. PATENT DOCUMENTS

| | | | | |
|---|---|---|---|---|
| 2,774,350 | A * | 12/1956 | Cleveland, Jr. ............... | 606/54 |
| 3,648,691 | A * | 3/1972 | Lumb et al. ................. | 606/279 |
| 4,289,123 | A * | 9/1981 | Dunn .......................... | 606/250 |
| 4,554,914 | A * | 11/1985 | Kapp et al. ................. | 606/86 A |
| 4,998,936 | A * | 3/1991 | Mehdian ..................... | 606/250 |
| 5,011,484 | A | 4/1991 | Breard | |
| 5,092,867 | A * | 3/1992 | Harms et al. ............... | 606/252 |
| 5,360,429 | A | 11/1994 | Jeanson et al. | |
| 5,380,325 | A * | 1/1995 | Lahille et al. ............... | 606/250 |
| 5,413,576 | A | 5/1995 | Rivard | |
| 5,474,551 | A * | 12/1995 | Finn et al. .................... | 606/264 |
| 5,507,745 | A | 4/1996 | Logroscino et al. | |
| 5,702,392 | A * | 12/1997 | Wu et al. ..................... | 606/264 |
| 6,136,000 | A | 10/2000 | Louis et al. | |
| 6,352,537 | B1 * | 3/2002 | Strnad ......................... | 606/276 |
| 6,402,749 | B1 * | 6/2002 | Ashman ...................... | 606/278 |
| 6,514,255 | B1 | 2/2003 | Ferree | |
| 6,610,091 | B1 | 8/2003 | Reiley | |
| 6,761,720 | B1 | 7/2004 | Senegas | |
| 6,811,567 | B2 | 11/2004 | Reiley | |
| 6,949,123 | B2 | 9/2005 | Reiley | |
| 7,048,736 | B2 * | 5/2006 | Robinson et al. .......... | 606/86 B |
| 7,335,203 | B2 * | 2/2008 | Winslow et al. ............. | 606/249 |
| 7,611,526 | B2 * | 11/2009 | Carl et al. .................... | 606/248 |
| 2003/0040746 | A1 | 2/2003 | Mitchell et al. | |
| 2003/0216736 | A1 | 11/2003 | Robinson et al. | |
| 2004/0006391 | A1 | 1/2004 | Reiley | |
| 2004/0049273 | A1 | 3/2004 | Reiley | |
| 2004/0049275 | A1 | 3/2004 | Reiley | |
| 2004/0049277 | A1 | 3/2004 | Reiley | |

(Continued)

Primary Examiner—Eduardo C Robert
Assistant Examiner—Jan Christopher Merene (57) ABSTRACT

Devices and methods for anchoring one or more elongate connecting members along the spinal column include a transverse linking member positionable through a spinous process in a generally orthogonal orientation to the sagittal plane. At least one coupling assembly is engageable about an end of the linking member extending from the spinous process. The elongate connecting member is engaged to the coupling assembly in a transverse orientation to the transverse linking member.

21 Claims, 5 Drawing Sheets

U.S. PATENT DOCUMENTS

| | | |
|---|---|---|
| 2004/0049278 A1 | 3/2004 | Reiley |
| 2004/0049281 A1 | 3/2004 | Reiley |
| 2004/0064140 A1* | 4/2004 | Taylor et al. .................. 606/61 |
| 2004/0249379 A1* | 12/2004 | Winslow et al. ............... 606/61 |
| 2005/0027361 A1 | 2/2005 | Reiley |
| 2006/0036246 A1* | 2/2006 | Carl et al. ..................... 606/61 |

* cited by examiner

SPINOUS PROCESS ANCHORING SYSTEMS AND METHODS

BACKGROUND

Spinal stabilization procedures are performed and include placement of devices between vertebral bodies in the disc space and/or along the spinal column. For example, varieties of inter-body fusion devices are widely used following partial or total discectomies to fuse adjacent vertebrae. Artificial disc devices can be placed in the disc space if motion preservation is desired. As an alternative to or as a supplement to interbody stabilization, stabilization devices are contemplated that include the attachment of plates, rods or tethers extradiscally along the vertebrae. Posterior stabilization devices can be engaged to the pedicles of the vertebrae. In certain situations, it is not desirable to engage anchors to the pedicle, but the need remains for an extradiscal posterior stabilization system.

SUMMARY

A spinous process anchoring system includes a transverse linking member positionable through the spinous process and at least one coupling assembly engageable to an end of the linking member extending from the spinous process. An elongate connecting member for spinal stabilization is engageable to the coupling assembly in a direction transversely oriented to the linking member.

According to another aspect, a spinous process anchoring system includes a primary transverse linking member including a length between opposite first and second ends sized to extend through a spinous process in a transverse orientation to a sagittal plane of the spinal column. The system also includes a secondary transverse linking member spaced from and extending generally parallel to the first primary transverse linking member and including a length between opposite first and second ends sized to extend through the spinous process. A pair of coupling assemblies each couple an elongate connecting member along the spinal column. At least one of the coupling assemblies is mounted to the first ends of the primary and secondary transverse linking members and the other of the coupling assemblies is mounted to at least the second ends of the primary transverse linking member. Engagement with the secondary transverse linking member resists rotation of the anchoring system about the axis of the primary transverse linking member.

In another aspect, a spinous process anchoring system includes a primary transverse linking member with a length between opposite first and second ends sized to extend through a spinous process in a transverse orientation to a sagittal plane of the spinal column. At least a portion of the primary transverse linking member includes an external thread profile for engaging the spinous process when positioned therethrough. The system also includes a coupling assembly having a coupling member body slidably received about one of the first and second ends of the primary transverse linking member. The coupling assembly includes a receiver configured to engage an elongate connecting member extending in a direction transversely to the primary transverse linking member. The system also includes an anchor engageable with the coupling assembly and the primary transverse linking member to secure the coupling assembly in position therealong.

In yet another aspect, a spinous process anchoring system includes a primary transverse linking member including a length between opposite first and second ends sized to extend through a spinous process in a transverse orientation to a sagittal plane of a spinal column. The system further includes a coupling assembly including a coupling member positioned about one of the first and second ends of the primary transverse linking member. The coupling assembly includes a receiver pivotally coupled to the coupling member. The receiver is configured to engage an elongate connecting member extending in a direction transversely to the primary transverse linking member. The receiver is pivotal relative to the primary transverse linking member to assume any one of a number of angular orientations relative thereto.

In another aspect, a transverse linking member for bi-laterally securing elongate connecting members along the spinal column is provided. The linking member includes a rod-shaped body extending between a first end and a second end. The body has a length between the first and second ends sized to extend through a spinous process in a generally orthogonal orientation to a sagittal plane of the spinal column. The body also includes a thread profile along a portion thereof between the first and second ends. The thread profile threadingly engages the spinous process when the body is positioned therethrough. The linking member also includes a first end portion extending from the threaded portion to the first end and a second end portion extending from the threaded portion to the second end. The first and second end portions each include a length sized to receive a coupling member thereon.

According to a further aspect, a method for anchoring an elongate connecting member along the spinal column includes: positioning a primary transverse linking member through a spinous process in a generally orthogonal orientation to a sagittal plane; positioning a secondary transverse linking member through the spinous process posteriorly of and generally parallel to the primary transverse linking member; positioning a coupling member about a portion of the primary transverse linking member extending from the spinous process; and contacting the coupling member with the secondary transverse linking member to resist rotation of the primary transverse linking member about its axis.

According to another aspect, a method for assembling a spinous process anchoring system includes: positioning a coupling member about an elongated primary transverse linking member; sliding the coupling member along the primary transverse linking member to contact an arm of the coupling member with an elongated secondary transverse linking member, the secondary transverse linking member being spaced from and extending generally parallel to the primary transverse linking member; and anchoring the coupling member to the primary transverse linking member.

These and other aspects will be discussed further below.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figures 1, 2:
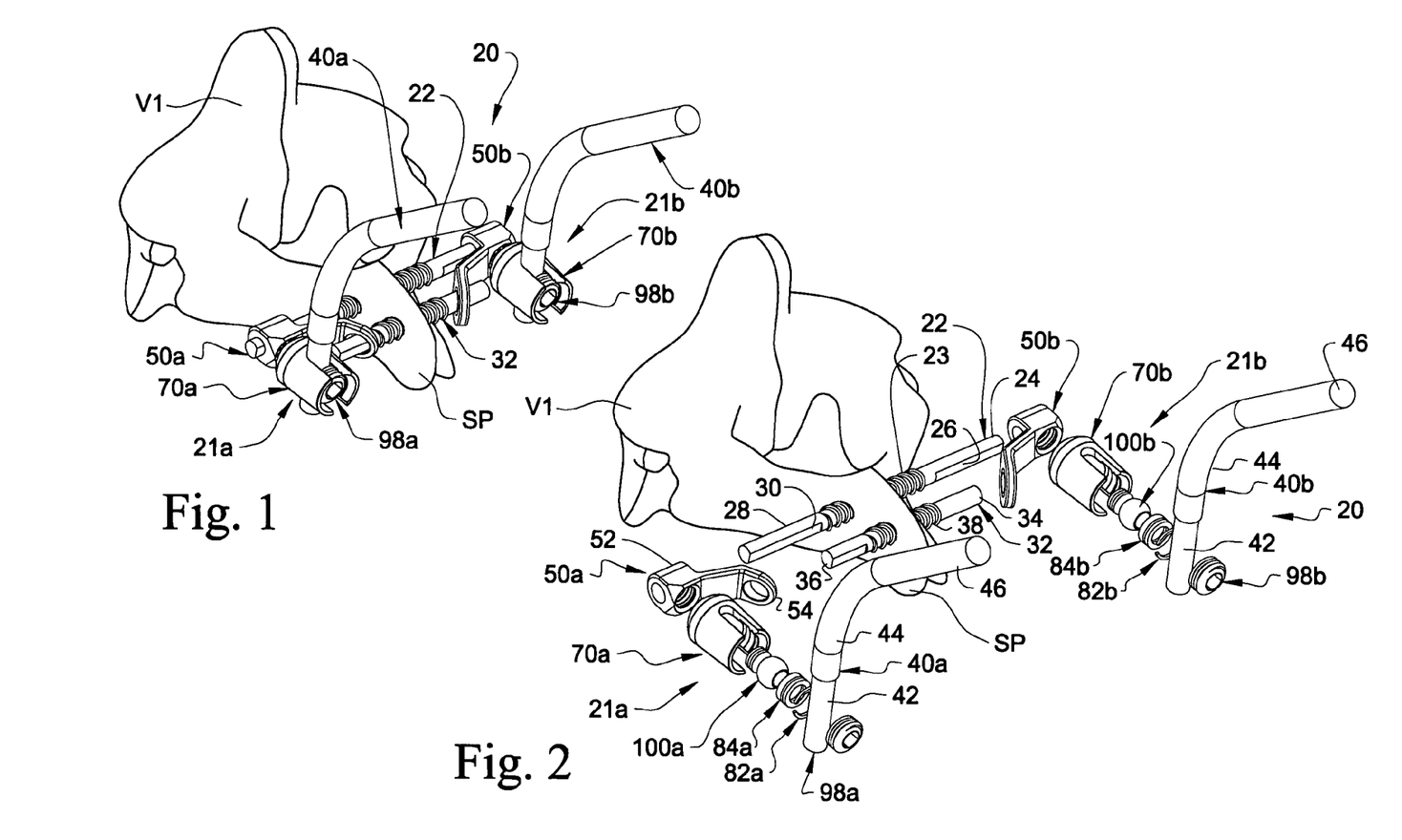
FIG. 1 is a perspective view of a spinous process anchoring system engaged to a spinous process of a vertebra.
FIG. 2 is an exploded view of the system of FIG. 1.
Figures 3, 4, 5:
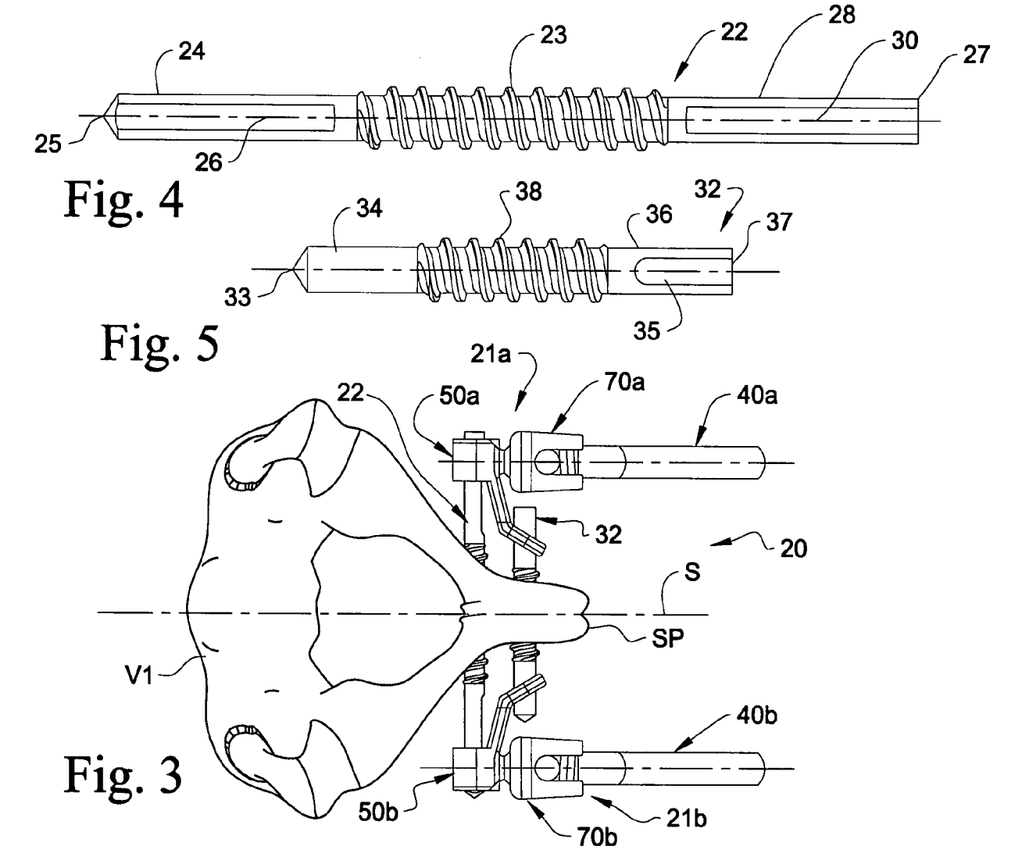
FIG. 3 is a bottom plan view of the system of FIG. 1.
FIG. 4 is an elevation view of a primary transverse linking member of the system of FIG. 1.
FIG. 5 is an elevation view of a secondary transverse linking member of the system of FIG. 1.

In FIGS. 1-3 there is shown a spinous process anchoring system 20 that is engageable to spinous process SP of vertebra V1. Anchoring system 20 includes a primary transverse linking member 22 extending through spinous process SP in a generally orthogonal orientation to sagittal plane S. Anchoring system 20 further includes coupling assemblies 21a, 21b engaged at opposite ends of primary transverse linking assembly 22. Elongate connecting members 40a, 40b are engageable with respective ones of the coupling assemblies 21a, 21b to secure the elongate connecting member to vertebra V1 in a direction that extends generally along the central axis of the spinal column and transversely to primary transverse linking member 22.

Coupling assemblies 21a, 21b can be identical to one another, and like components are designated with the same reference numeral, with components associated with coupling assembly 21a including an "a" after the reference numeral and with components associated with coupling assembly 21b including a "b" after the reference number. The "a" and "b" components are also collectively and individually also referred to herein by dropping the "a" and "b" designation. It should be further understood that system 20 may be employed with only one of either of the coupling assemblies 21a, 21b.

Coupling assemblies 21a, 21b include the respective receiver 70a, 70b mounted to primary transverse linking member 22 by a coupling member 50. Receiver 70 can be pivotal relative to primary transverse linking member 22 and the respective coupling member 50 to facilitate placement and connection of connecting member 40 thereto. In another embodiment, receiver 70 can be formed as a non-pivoting portion of the coupling assembly. In the illustrated embodiment of FIGS. 1-3, receiver 70 is pivotally coupled to a coupling member 50 with anchor 100. Anchor 100 is further configured to engage primary transverse linking member 22 and secure coupling member 50 in position thereon.

Coupling member 50 includes a hub portion 52 defining a passage that allows coupling member 50 to be positioned about primary transverse linking member 22. To provide the desired fit with the vertebral anatomy, coupling member 50 can be slidably adjustable in its positioning along linking member 22 and then secured in the desired position with anchor 100. Other embodiments contemplate that coupling member 50 is not adjustable in position along linking member 22, but rather is engageable in a single position therealong. Coupling member 50 further includes an arm 54 extending medially from hub portion 52 that is positioned about an adjacent end of secondary transverse linking member 32 projecting from spinous process SP. The engagement of arm 54 to secondary transverse linking member 32 resists rotation of primary transverse linking member 22 about its axis when coupling member 50 is secured to primary transverse linking member 22.

Primary transverse linking member 22 is shown in isolation in FIG. 4. Primary transverse linking member 22 includes an elongated, rod-like body extending from a first end 25 to an opposite second end 27. A first end region 24 extends medially from first end 25 and a second end region 28 extends medially from second end 27. End regions 24, 28 are joined to one another by a medial region 23 defining an external thread profile therealong. Medial region 23 can threadingly engage the bone of the spinous process SP when positioned therethrough. A pointed tip at first end 25 can facilitate placement of transverse linking member through spinous process SP. It is contemplated that a bore can be formed in spinous process SP to facilitate insertion of linking member 22 therethrough. Alternatively, linking member 22 can self-bore the spinous process when pushed therethrough. Medial region 23 can threadingly engage the bony material thereabout to secure linking member 22 in position. Other embodiments contemplate other coupling arrangements for engaging primary transverse linking member 22 to the spinous process, including spikes, knurlings, ridges, clamps, fasteners, frictional engagement, expandable portions, collars, and sleeves, for example.

When medial region 23 is engaged to spinous process SP as shown in FIGS. 1-3, end regions 24, 28 extend from respective sides of spinous process SP on opposite sides of sagittal plane S. Each of the regions 24, 28 can each include a respective flat surface portion 26, 30 formed therealong, the purpose for which will be discussed further below. Embodiments without flat surface portions 26, 30 are also contemplated. Coupling assemblies 21a, 21b are engageable to respective ones of end regions 28, 24.

One embodiment of system 20 includes a secondary transverse linking member 32 engageable by coupling assemblies 21a, 21b to resist coupling assemblies 21a, 21b and primary transverse linking member 22 from rotating about its axis. Secondary transverse linking member 32 is shown in isolation in FIG. 5, and includes an elongated, rod-like body extending from a first end 33 to an opposite second end 37. A first end region 34 extends medially from first end 33 and a second end region 36 extends medially from second end 37. End regions 34, 36 are joined to one another by a medial region 38 defining an external thread profile therealong. Medial region 38 can threadingly engage the bone of the spinous process SP when positioned therethrough. A pointed tip at first end 33 can facilitate placement of transverse linking member through spinous process SP. Relative to the length of primary transverse linking member 22 between ends 25, 27, secondary transverse linking member 32 includes a shorter length between ends 33, 37 so as to not interfere with the positioning of coupling assemblies 21a, 21b about primary transverse linking member 22.

It is contemplated that a bore can be formed in spinous process SP to facilitate insertion of secondary transverse linking member 32 therethrough. Alternatively, linking member 32 can self-bore the spinous process. Medial region 38 can threadingly engage the bony material thereabout to secure linking member 32 in position. Other embodiments contemplate other coupling arrangements for engaging secondary transverse linking member 32 to the spinous process, including spikes, knurlings, ridges, clamps, fasteners, frictional engagement, expandable portions, collars, and sleeves, for example.

When medial region 38 is engaged to spinous process SP as shown in FIGS. 1-3, secondary transverse linking member 32 is located posteriorly of and extends generally parallel to primary transverse linking member 22. Coupling assemblies 21a, 21b each include an arm 54 that extends along linking member 22 toward the spinous process SP. The medial end of the arm 54 is offset posteriorly toward linking member 32 for contact therewith. In the illustrated embodiment, arms 54 each include a medially-laterally extending bore 60 that receives the respective end regions 34, 36 of secondary transverse linking member 32 therethrough. Arms 54 contact secondary transverse linking member 32 to prevent the respective coupling assembly 21a, 21b and primary transverse linking member 22 from rotating about the axis of primary transverse linking member 22.

Figure 6A:
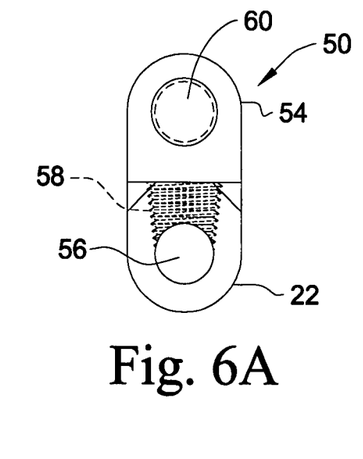
FIGS. 6A and 6B are front and side elevation views of a coupling member of the system of FIG. 1.
Figure 6B:
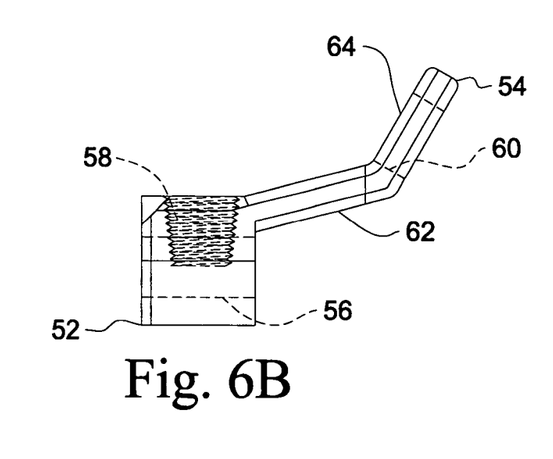

One embodiment coupling member 50 of coupling assemblies 21a, 21b is shown in FIGS. 6A and 6B. Coupling member 50 includes a coupling body having hub portion 52 positionable about linking member 22 and arm 54 extending from a medial end of hub portion 52. Hub portion 52 includes a sleeve-like configuration with a central passage 56 extending therethrough. Arm 54 extends from a medial end of hub portion 52 in the medial direction and is located on the posterior side thereof when coupling member 50 is positioned on linking member 22 in its operative position. Arm 54 includes a first medially extending portion 62 and a second posteriorly extending portion 64 defining bore 60. The angulation of second portion 64 orients the opening of bore 60 in the medial-lateral direction toward the respective adjacent end of secondary transverse linking member 32, allowing arm 54 to be positioned thereover.

Coupling member 50 further includes a threaded bore 58 in communication with central passage 56. Threaded bore 58 is threadingly engageable to respective ones of the anchors 100a, 100b. The respective anchor 100 is engageable in bore 58 and into contact with the flat surface portion of primary transverse linking member 22 to engage coupling member 50 thereto in a desired position therealong.

Figure 7:
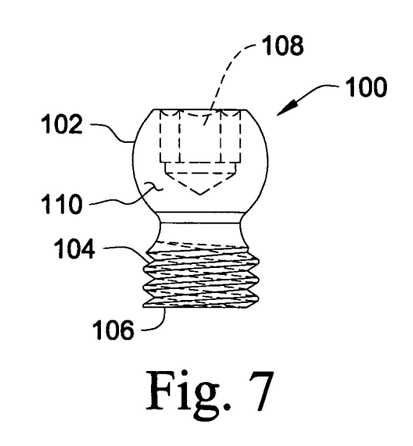
FIG. 7 is an elevation view of an anchor of the system of FIG. 1.

As shown in FIG. 7, anchor 100 includes a proximal head 102 and a distally extending threaded shank 104 extending from head 102. Shaft 104 includes a distal end 106 that abuttingly engages the respective flat surface portion 26, 30 along primary transverse linking member 22 to securing coupling member 50 thereto. Other embodiments contemplate a pointed distal end that penetrates linking member 22, or a distal end that is received in a recess or receptacle in linking member 22. Head 102 can be enlarged relative to shaft 104, and includes a rounded outer surface 110 to facilitate pivoting movement of receiver 70 thereabout, as discussed further below. A tool engaging recess 108 in the proximal end of head 102 receives a driving tool to allow application of a driving force to anchor 100 and facilitate securing of distal end 106 against linking member 22.

Figure 8:
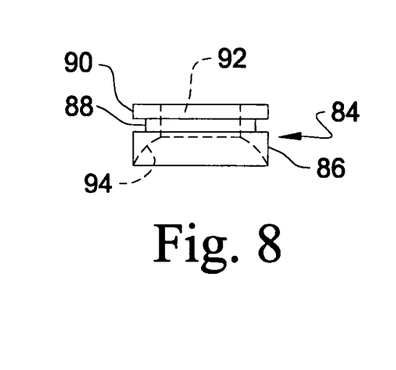
FIG. 8 is an elevation view of a crown of the system of FIG. 1.

Coupling assemblies 21a, 21b can further each include a crown 84a, 84b, respectively, shown in FIG. 8. Crowns 84a, 84b are positioned about the head 102 of the respective anchors 100a, 100b. Crowns 84a, 84b are axially retained in the respective receiver 70a, 70b by C-rings 82a, 82b. Crown 84 includes a sleeve-like body 86 defining a circumferential groove 88 for receiving ring 82 therein. Body 86 includes a bore therethrough including a flared distal portion 94 shaped generally complementary to the proximal end of head 102 of anchor 100. The bore further includes a proximal portion 92 opening at proximal end 90. A driving tool can be positioned through proximal portion 92 and into engagement with tool engaging recess 108 of head 102 to facilitate securing it to linking member 22.

Figure 9:
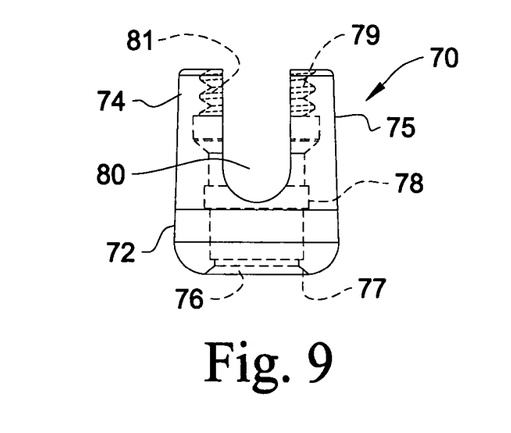
FIG. 9 is an elevation view of a receiver of the system of FIG. 1.

Each of the coupling assemblies 21a, 21b also includes receiver 70a, 70b to couple the respective connecting member 40a, 40b thereto. As shown in FIG. 9, receiver 70 includes a U-shaped saddle-like configuration having a lower distal portion 72 and a pair of arms 74, 75 extending proximally from distal portion 72. Distal portion 72 defines a receptacle 76 opening at a distal end thereof through which shaft 104 of anchor 100 extends. A lip 77 or other suitable coupling arrangement adjacent the lower opening of receptacle 76 retains head 102 of anchor 100 in receptacle 76 while permitting receiver 70 to pivot about head 102 of anchor 100. Inner groove 78 about receptacle 76 receives C-ring 82 to axially restrain crown 84 in receptacle 76.

Arms 74, 75 define U-shaped passage 80 therebetween which is sized to receive connecting member 40 therein. Arms 74, 75 can include internal threads 81, 79, respectively, for engagement with a respective one of the engaging members 98a, 98b. Engaging members 98a, 98b each include an externally threaded configuration that threadingly engages the respective arms 74, 75. As engaging members 98a, 98b are engaged to the respective receiver 70a, 70b, the engaging member contacts the respective connecting member 40a, 40b and forces it into contact with the respective crown 84a, 84b, which in turn forces the respective crown 84a, 84b onto the adjacent head 102a, 102b of anchor 100a, 100b. As anchors 100a, 100b are pressed into engagement with the respective receiver 70a, 70b, the anchors and receivers lock in position relative to one another.

Other embodiments contemplated other coupling arrangements between receiver 70 and coupling member 50. For example, anchor 100 can be retained in receiver 70 with a snap ring, collar, or can be integrally formed therewith. Crown 84 can be omitted and the elongate connecting member can directly contact the head of anchor 100. Engaging member 98 can be in the form of a nut that engages external threads along receiver 70, or include one or more components engageable internally and/or externally to receiver 70. Receiver 70 can be configured to receive the connecting member in a side-loading or bottom-loading manner. In another form, receiver 70 provides a post and the connecting member is positioned thereover. In another form, a second coupling mechanism can be engaged to receiver 70, and the connecting member is engaged to the second coupling mechanism.

Figures 10, 11:
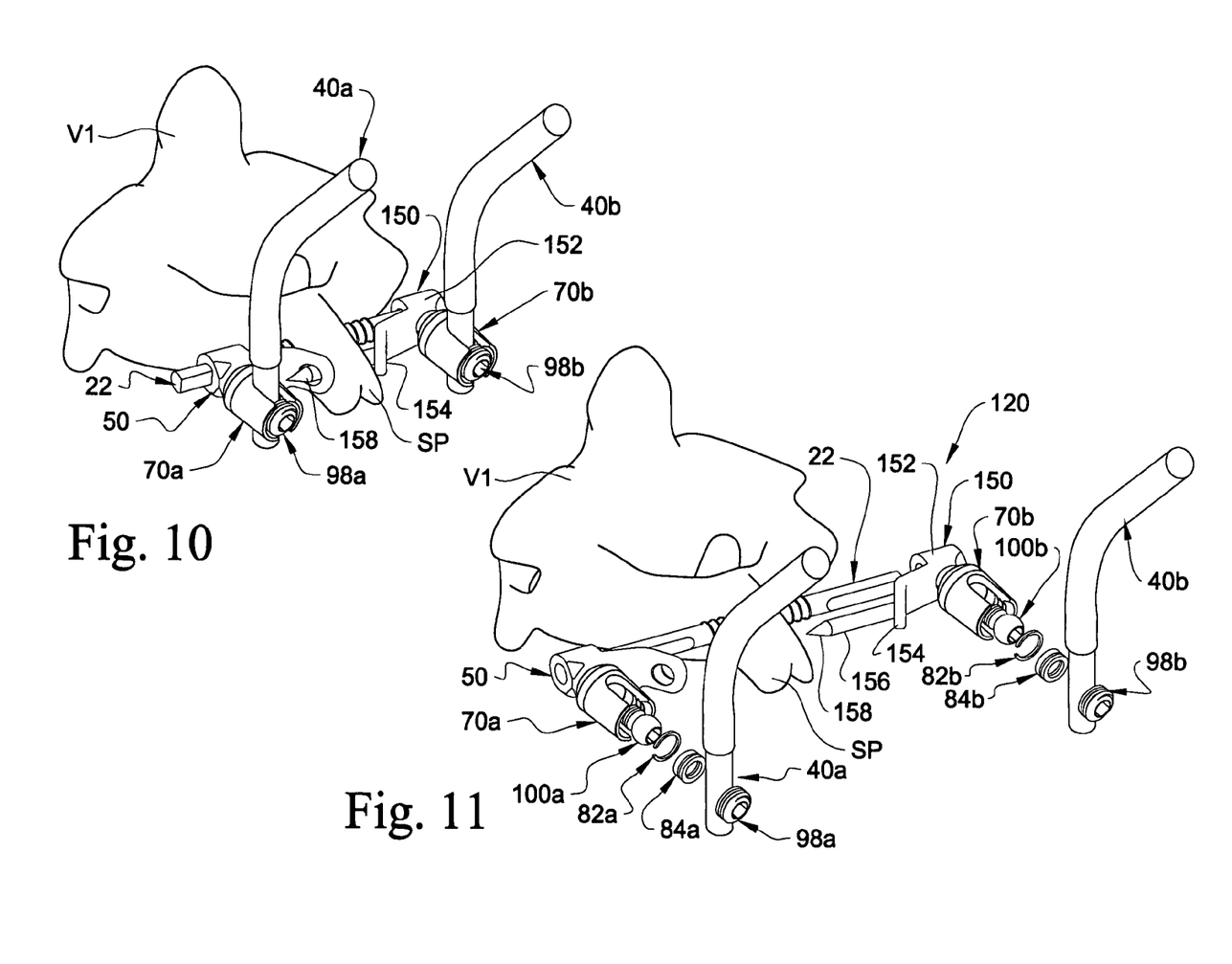
FIG. 10 is a perspective view of another embodiment spinous process anchoring system engaged to a spinous process of a vertebra.
FIG. 11 is an exploded view of the system of FIG. 10.
Figure 12:
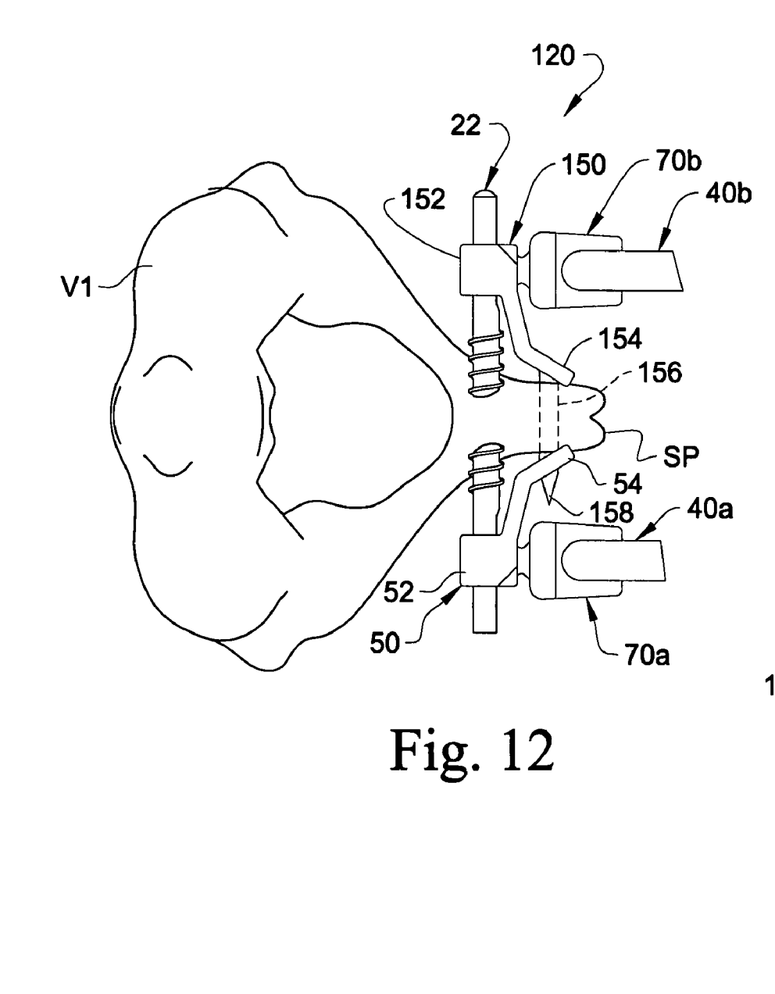
FIG. 12 is a top plan view of the system of FIG. 10.

FIGS. 10-12 illustrate another embodiment spinous process anchoring system 120. Anchoring system 120 is similar to anchoring system 20 discussed above, and like elements are designated with like reference numerals. Anchoring system 120 differs from anchoring system 20 in that one of the coupling members, designated as coupling member 150, includes a secondary transverse linking member 156 integrally formed with an arm portion 154. Arm portion 154 extends from a hub portion 152 that is positionable about primary transverse linking member 22. The integral secondary transverse linking member 156 includes a pointed end 158 to facilitate placement through spinous process SP. Engagement of linking member 156 with spinous process SP prevents coupling member 150 and primary transverse linking member 22 from rotating about the axis of primary transverse linking member 22. Coupling member 50, on the side of the spinous process opposite coupling member 150, includes arm 54 that is positioned about the end of linking member 156 extending from spinous process SP to also resist rotation of the assembly about the axis of primary transverse linking member 22.

In yet another embodiment, the transverse linking member is provided by one or more bone screws that engage the arms of the respective coupling member or members to the spinous process posteriorly of the primary transverse linking member. The bone screw or screws resist the anchoring assembly from rotating about the axis of the primary transverse linking member.

Figure 13:
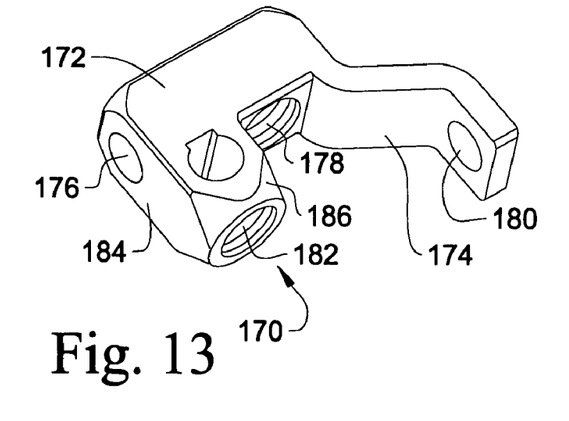
FIG. 13 is a perspective view of another embodiment coupling member useable with the spinous process anchoring systems herein.

Referring now to FIG. 13, another embodiment coupling member 170 is shown. Coupling member 170 includes a hub portion 172 defining a central passage 176 for receiving primary transverse linking member 22 in a manner similar to coupling member 50 discussed above. Hub portion 172 includes an engaging bore 178 extending therethrough to receive an anchor to engage coupling member 170 to linking member 22. Coupling member 170 further includes an arm 174 extending from a medial end of hub portion 172. Arm 174 is contoured to extend along the lateral side of spinous process SP so that bore 180, adjacent an outer end thereof, is oriented in the medial-lateral direction and can be positioned about secondary transverse linking member 32.

Coupling member 170 further includes an integral receiver portion 186 defining a passage 184 extending in the direction of the spinal column. A connecting member can be positioned through passage 184 and engaged therein with an engaging member (such as engaging member 98 discussed above) in transverse bore 182. The engaging member can restrain the connecting member relative to coupling member 170 while coupling member 170 provides a uni-axial relationship between the receiver portion 186 and linking member 22.

Figure 14:
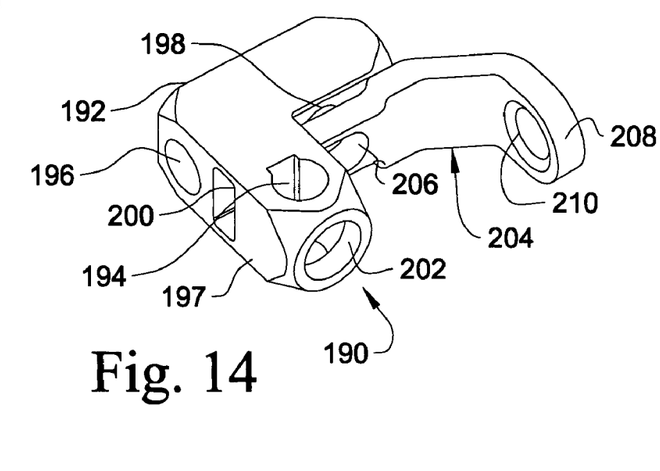
FIG. 14 is a perspective view of another embodiment coupling member useable with the spinous process anchoring systems herein.

Referring now to FIG. 14, there is shown another embodiment coupling member for the coupling assembly. Coupling member 190 is similar to coupling member 170 and provides a uni-axial arrangement between the connecting member and the linking member 22. Coupling member 190 includes a hub portion 192 defining a central passage 196 for receiving primary transverse linking member 22 in a manner similar to coupling member 50 discussed above. Hub portion 192 includes an engaging bore 198 extending therethrough to receive an anchor to engage coupling member 190 to linking member 22. Coupling member 190 further includes an integral receiver portion 197 defining a passage 194 extending in the direction of the spinal column. A connecting member can be positioned through passage 194 and engaged therein with an engaging member (such as engaging member 98 discussed above) in transverse bore 202. The engaging member can restrain the connecting member relative to coupling member 190 while coupling member 190 provides a uni-axial relationship between the receiver portion and linking member 22.

Coupling member 190 further includes an arm 204 that is formed as a separate component from hub portion 192. Arm 204 is contoured to extend along the lateral side of the spinous process SP and along the posterior side of hub portion 192. Arm 204 includes a bore 210 adjacent outer end 208 that receives an adjacent end of secondary transverse linking member 32, a bone screw extending through or into the spinous process, or some other engaging member. The opposite end of arm 204 is slidably and adjustably received in passage 200 extending medially and laterally between hub portion 192 and receiving portion 197. Arm 204 includes a slot 206. Slot 206 is alignable with engaging bore 198 and is configured to permit passage of the anchor to engage linking member 22 to secure hub portion 192 in position therealong. Arm 204 contacts hub portion 192 in passage 200 so that arm 204 and hub portion 192 do not rotate relative to one another, and so that the anchoring of arm 204 to the spinous process prevents hub portion 192 and/or the primary transverse linking member to which it is engaged from rotating about the axis of the linking member.

While one vertebra V1 is shown in the illustrated embodiments, it is contemplated that multiple vertebrae may be involved in a stabilization procedure. A corresponding anchoring system 20 can be provided for each involved vertebra, or one or more other of the involved vertebrae may employ some other suitable system or device for securing the connecting member thereto. In one example, the elongate connecting members 40a, 40b can be sized to extend along one or more vertebral levels, and can be engaged to at least one of the vertebra along the stabilized vertebral levels with transverse linking member 22 and coupling assemblies 21. Additional anchoring systems 20 or other suitable coupling systems are provided for the other vertebral levels. The illustrated embodiments show bi-lateral stabilization with connecting members along the spinal column on each side of sagittal plane S. Systems that employ uni-lateral stabilization are also contemplated.

Vertebra V1 in the illustrated embodiment can be vertebra C2 of the cervical region of the spinal column. Connecting members 40a, 40b can be elongated rods with a curved region 44 that is curved posteriorly toward superior end 46 in order to position superior end 46 along the occiput. Inferior end 42 can have a reduced diameter or profile to facilitate receipt in the passage of the respective receiver 70a, 70b. One specific application contemplates occipito-cervical stabilization for occipito-cervical fusion procedures. For example, occipito-cervical fusion can be required in pediatric patients with Down Syndrome. The size of the cervical vertebrae, in particular the pedicles thereof, may make pedicle screw insertion unfeasible. This problem can also be present in children with small bony structure or in situations where the pedicles cannot be entered with a bone screw. Resorting to pedicle hooks for securing the connecting member along the spinal column requires additional levels of fixation below C2. Anchoring system 20 can be employed to anchor the elongate connecting member or members to the spinous process of C2 without the need to extend the anchoring system to additional vertebral levels.

Anchoring system 20 also has application in other procedures not involving occipito-cervical fixation and in all patients requiring posterior spinal stabilization. Anchoring system 20 can be employed with one or more vertebrae along the spinal column where pedicle screw engagement is not desired or preferred. Applications in the cervical, thoracic, lumbar and sacral regions of the spine are contemplated. The connecting members need not be posteriorly curve rods as shown. The connecting members can be linear, curved, rigid, flexible, elastic, comprised of multiple components, and made from any suitable biocompatible material or combinations of materials. The connecting members can have varying cross-sectional properties along their lengths. The connecting members can be in the form of spinal rods, plates, cables, tethers, cords, bumpers, and springs, for example.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinous process anchoring system, comprising:
a primary transverse linking member including a length extending along an axis between opposite first and second ends sized to extend through a spinous process of a first vertebra in a transverse orientation to a sagittal plane of the spinal column;
a secondary transverse linking member positionable to be spaced from and extending generally parallel to said first primary transverse linking member and including a length between opposite first and second ends sized to extend through the spinous process; and
a pair of coupling assemblies, each including a coupling member and a receiver with a passage, at least one of said coupling assemblies being mounted to said first ends of each of said primary and secondary transverse linking members and the other of said coupling assemblies being mounted to at least said second end of said primary transverse linking member, wherein said engagement with said secondary transverse linking member resists rotation of the anchoring system about the axis of the primary transverse linking member; and
a pair of elongate connecting members each received in said passage of said receiver of a respective one of said pair of coupling assemblies in a transverse orientation to said primary transverse linking member, said connecting members including a length extending from said passage sized to extend to at least one of a second vertebra and an occiput, wherein said first and second ends of said second transverse linking member are located between said receivers of said pair of coupling assemblies, wherein said coupling member of said coupling assembly includes a hub portion positioned about said respective end of said primary transverse linking member and an arm extending from said hub portion, said arm defining a bore for receiving said respective end of said secondary transverse linking member, wherein said coupling assembly includes an anchor having a head pivotally captured in a lower portion of said receiver and a threaded shaft extending from said head through a lower opening of said receiver, said threaded shaft threadingly engaging a bore in said coupling member and contacting said primary transverse linking member to secure said coupling member in position therealong and to pivotally couple said receiver to said coupling member.

2. The system of claim 1, wherein said length of said primary transverse linking member is greater than said length of said secondary transverse linking member.

3. The system of claim 1, wherein said primary transverse linking member includes an externally threaded portion between said first and second ends for threadingly engaging the spinous process.

4. The system of claim 1, wherein said first ends of each of said primary and secondary transverse linking members are pointed.

5. The system of claim 1, wherein said primary transverse linking member includes a flat surface extending therealong along a portion of the length thereof from respective ones of said first and second ends.

6. The system of claim 5, wherein said primary transverse linking member includes said flat surface extending from each of said first and second ends along said portion of said length, said flat surfaces extending toward one another from said first and second ends and said primary transverse linking member includes an externally threaded region between said flat surfaces.

7. A spinous process anchoring system, comprising: a primary transverse linking member including a length extending along an axis between opposite first and second ends sized to extend through a spinous process in a transverse orientation to a sagittal plane of the spinal column;
a secondary transverse linking member positionable to be spaced from and extending generally parallel to said first primary transverse linking member and including a length between opposite first and second ends sized to extend through the spinous process; and
a pair of coupling assemblies, each for coupling an elongate connecting member along the spinal column, at least one of said coupling assemblies being mounted to said first ends of each of said primary and secondary transverse linking members and the other of said coupling assemblies being mounted to at least said second end of said primary transverse linking member, wherein said engagement with said secondary transverse linking member resists rotation of the anchoring system about the axis of the primary transverse linking member, wherein each of said coupling assemblies includes:
a coupling member including a hub portion positioned about said respective end of said primary transverse linking member and an arm extending from said hub portion, said arm defining a bore for receiving said respective end of said secondary transverse linking member; and
a receiver extending from coupling member, said receiver being engageable to the elongate connecting member, wherein said receiver defines a passage and said elongate connecting member is a rod positionable in said passage and engageable therein with a set screw engaged to said receiver,
wherein said receiver is pivotally coupled to said coupling member,
wherein said coupling assembly includes an anchor having a head pivotally captured in a lower portion of said receiver and a threaded shaft extending from said head through a lower opening of said receiver, said threaded shaft threadingly engaging a bore in said coupling member and contacting said primary transverse linking member to secure said coupling member in position therealong and to pivotally couple said receiver to said coupling member.

8. The system of claim 7, further comprising a crown in said receiver about said head of said multi-axial anchor, said receiver defining an upper portion for receiving said elongate connecting in contact with said crown.

9. A spinous process anchoring system, comprising: a primary transverse linking member including a length extending along an axis between opposite first and second ends sized to extend through a spinous process in a transverse orientation to a sagittal plane of the spinal column;
a secondary transverse linking member positionable to be spaced from and extending generally parallel to said first primary transverse linking member and including a length between opposite first and second ends sized to extend through the spinous process; and
a pair of coupling assemblies, each for coupling an elongate connecting member along the spinal column, at least one of said coupling assemblies being mounted to said first ends of each of said primary and secondary transverse linking members and the other of said coupling assemblies being mounted to at least said second end of said primary transverse linking member, wherein said engagement with said secondary transverse linking member resists rotation of the anchoring system about the axis of the primary transverse linking member, wherein each of said coupling assemblies includes:
a coupling member including a hub portion positioned about said respective end of said primary transverse linking member and an arm extending from said hub portion, said arm defining a bore for receiving said respective end of said secondary transverse linking member, said coupling member further including a receiver portion defining a passage transversely oriented to said primary transverse linking member for receiving the elongate connecting member therethrough, wherein said first and second ends of said secondary transverse linking member are located between said receivers of said coupling members, wherein said coupling assembly includes an anchor having a head pivotally captured in a lower portion of said receiver portion and a threaded shaft extending from said head through a lower opening of said receiver portion, said threaded shaft threadingly engaging a bore in said coupling member and contacting said primary transverse linking member to secure said coupling member in position therealong and to pivotally couple said receiver portion to said coupling member.

10. A spinous process anchoring system, comprising: a primary transverse linking member including a length between opposite first and second ends sized to extend through a spinous process in a transverse orientation to a sagittal plane of the spinal column, at least a portion of said primary transverse linking member including an external thread profile for engaging the spinous process when positioned therethrough;
a coupling assembly including a coupling member at one of said first and second ends of said primary transverse linking member, said coupling assembly including a receiver configured to engage an elongate connecting member extending in a direction transversely to said primary transverse linking member; and
an anchor including a distal end in abutting engagement with said primary transverse linking member and a head opposite said distal end and positioned in said receiver to secure said receiver to said coupling member and said coupling member to said primary transverse linking member, wherein said anchor includes a threaded shaft extending from said head through a lower opening of said receiver to said distal end, said threaded shaft threadingly engaging a bore in said coupling member with said distal end contacting said primary transverse linking member to secure said coupling member in position therealong and to pivotally couple said receiver to said coupling member;
a secondary transverse linking member positionable to be spaced from and extending generally parallel to said first primary transverse linking member, wherein said coupling member of said coupling assembly includes a hub portion positioned about said respective end of said primary transverse linking member and an arm extending from said hub portion, said arm defining a bore for receiving said respective end of said secondary transverse linking member.

11. The system of claim 10, wherein said receiver includes a pair of arms extending from said lower portion, said pair of arms defining a passage therebetween for receiving the elongate connecting member therein.

12. A spinous process anchoring system, comprising: a primary transverse linking member including a length between opposite first and second ends sized to extend through a spinous process in a transverse orientation to a sagittal plane of the spinal column, at least a portion of said primary transverse linking member including an external thread profile for engaging the spinous process when positioned therethrough;
a coupling assembly including a coupling member body at one of said first and second ends of said primary transverse linking member, said coupling assembly including a receiver configured to engage an elongate connecting member extending in a direction transversely to said primary transverse linking member; and
an anchor engageable with said coupling assembly and said primary transverse linking member to secure said coupling assembly to said primary transverse linking member, wherein said coupling member includes an arm extending along said primary transverse linking member to an outer end of said arm, said outer end being engageable to the spinous process at a location spaced from said primary transverse linking member;
a secondary transverse linking member positionable to be spaced from and extending generally parallel to said first primary transverse linking member, wherein said coupling member of said coupling assembly includes a hub portion positioned about said respective end of said primary transverse linking member and said arm extends from said hub portion, said arm defining a bore for receiving said respective end of said secondary transverse linking member, wherein said anchor has a head pivotally captured in a lower portion of said receiver and a threaded shaft extending from said head through a lower opening of said receiver, said threaded shaft threadingly engaging a bore in said coupling member and contacting said primary transverse linking member to secure said coupling member in position therealong and to pivotally couple said receiver to said coupling member.

13. The system of claim 12, wherein said secondary transverse linking member includes a length sized to extend through the spinous process and has an end extending from the spinous process, said outer end of said arm defining a bore adjacent said outer end for receiving said end of said secondary transverse linking member.

14. The system of claim 12, further comprising:
a second coupling assembly including a coupling member slidably received about the other of said first and second ends of said primary transverse linking member, said second coupling assembly including a receiver configured to receive a second elongate connecting member in a direction extending transversely to said primary transverse linking member; and
an anchor assembly engageable with said second coupling assembly and said primary transverse linking member to secure said second coupling assembly in position therealong.

15. A spinous process anchoring system, comprising: a primary transverse linking member including a length extending along an axis between opposite first and second ends sized to extend through a spinous process in a transverse orientation to a sagittal plane of a spinal column; and
a coupling assembly including a coupling member positioned about one of said first and second ends of said primary transverse linking member, said coupling assembly including a receiver pivotally coupled to said coupling member, said receiver being configured to engage an elongate connecting member extending in a direction transversely to said primary transverse linking member, wherein said receiver is pivotal relative to said primary transverse linking member to assume any one of a number of angular orientations relative thereto; and an anchor including a distal end in abutting engagement with said primary transverse linking member and a head opposite said distal end and positioned in said receiver to secure said receiver to said coupling member and said coupling member to said primary transverse linking member;

a secondary transverse linking member positionable to be spaced from and extending generally parallel to said first primary transverse linking member, wherein said coupling member of said coupling assembly includes a hub portion positioned about said respective end of said primary transverse linking member and an arm extending from said hub portion, said arm defining a bore for receiving said respective end of said secondary transverse linking member, wherein said head of said anchor is pivotally captured in a lower portion of said receiver and said anchor includes a threaded shaft extending from said head through a lower opening of said receiver, said threaded shaft threadingly engaging a bore in said coupling member and contacting said primary transverse linking member to secure said coupling member in position therealong and to pivotally couple said receiver to said coupling member.

16. The system of claim 15, wherein said anchor pivotally couples said receiver to said coupling member.

17. The system of claim 15, wherein said secondary transverse linking member is spaced from and extends generally parallel to said primary transverse linking member, wherein said coupling member contacts said secondary transverse linking member to prevent rotation of the anchoring system about the axis of said primary transverse linking member.

18. A method for assembling a spinous process anchoring system, comprising:

positioning a coupling member about an elongated primary transverse linking member; sliding the coupling member along the primary transverse linking member to contact an arm of the coupling member with an elongated secondary transverse linking member, the secondary transverse linking member being spaced from and extending generally parallel to the primary transverse linking member, wherein the primary transverse linking member and the secondary transverse linking member each extend through a spinous process of a spinal column; and anchoring the coupling member to the primary transverse linking member; wherein the coupling member includes a hub portion positioned about the primary transverse linking member and the arm extends from the hub portion, the arm defining a bore for receiving an end of the secondary transverse linking member, the coupling member further including a receiver extending therefrom, wherein the coupling assembly includes an anchor having a head pivotally captured in a lower portion of the receiver and a threaded shaft extending from the head through a lower opening of the receiver, the threaded shaft threadingly engaging a bore in the coupling member and contacting the primary transverse linking member to secure the coupling member in position therealong and to pivotally couple the receiver to the coupling member; and engaging an elongate connecting member to the receiver.

19. The method of claim 18, wherein anchoring the coupling member include pivotally coupling a receiver to the coupling member.

20. The method of claim 19, further comprising engaging an elongate connecting member to the receiver with the elongate connecting member extending transversely to the primary transverse linking member.

21. The method of claim 20, wherein engaging the elongate connecting member locks the receiver in position relative to the coupling member.

* * * * *